United States Patent
Pont-Kingdon et al.

(10) Patent No.: US 7,563,572 B2
(45) Date of Patent: Jul. 21, 2009

(54) METHOD FOR LONG RANGE ALLELE-SPECIFIC PCR

(75) Inventors: Genevieve Pont-Kingdon, Salt Lake City, UT (US); Elaine Lyon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 255 days.

(21) Appl. No.: 11/194,367

(22) Filed: Aug. 1, 2005

(65) Prior Publication Data

US 2007/0184457 A1 Aug. 9, 2007

Related U.S. Application Data

(60) Provisional application No. 60/598,226, filed on Aug. 2, 2004.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33
(58) Field of Classification Search .............. 435/6, 435/91.2; 536/24.33
See application file for complete search history.

(56) References Cited

OTHER PUBLICATIONS

Michalatos-Beloin et al. Molecular haplotyping og genetic markers 10 kb apart by allele-specific long-range PCr. Nucleic Acids Res., vol. 24, No. 23, pp. 4865-4867, 1996.*
Friedman et al. Rapid characterization of the variable length polythymidine tract in the CFTR gene: Association of the 5T allele with selected CTR mutations and its incidence in atypical sinopulmonary disease. Human Mutation, vol. 10, pp. 108-115, 1997.*
Inbar, E et al. An efficient haplotyping method with DNA pools. Nucleic Acids Research, vol. 30, No. 15, p. e76 1-5, 2002.*
Latorra, D et al. Enhanced allele-specific PCR discrimination in SNP genotyping using 3'locked nucleic acid (LNA) primers. Human Mutation, vol. 22, pp. 79-85, 2003.*
Pont-Kingdon, G et al. Long-range (17.7 kb) allele-specific polymerase chain reaction method for direct haplotying of R117H and IVS-8 mutations of the cyctic fibrosis transmembrane regulator gene. J.Molecular Diagnostics, vol. 6, No. 3, Aug. 1, 2004.*
Cheng, S et al. Effective amplification of long targets from cloned inserts and human genomic DNA. PNAS, vol. 91, pp. 5695-5699, 1994.*

* cited by examiner

*Primary Examiner*—Suryaprabha Chunduru
(74) *Attorney, Agent, or Firm*—Christopher L. Wight; Brinks Hofer Gilson & Lione (57) ABSTRACT

The present invention is directed to a method and kit for determining the molecular haplotype of a gene in a diploid DNA sample. The method discriminates between two haplotypes on the basis of a difference of one or more nucleotides using allele-specific PCR amplification in combination with long range PCR, using a DNA polymerase enzyme having 3'→5' exonuclease activity, using annealing temperature conditions sufficiently greater than the predicted annealing temperature (Tm) to effect selective hybridization and extension of an allele-specific extension primer to the target allele relative to the variant allele. The present invention is particularly useful, for example, to determine the haplotype of a gene having multi-allelic genetic loci separated by a distance in which accurate PCR amplification of a single fragment containing the multiple genetic loci cannot be performed without using a DNA polymerase enzyme having 3'→5' exonuclease activity, generally about 5 kilobases or more.

5 Claims, 2 Drawing Sheets

SEQUENCE LISTING

<160> NUMBER OF SEQ ID NOS: 6

<210> SEQ ID NO 1
<211> LENGTH: 44
<212> TYPE: DNA
<213> ORGANISM: Homo sapiens

<400> SEQUENCE: 1
ctattgttat tgttttgttt tgctttctca ataattccc caaa     44

<210> SEQ ID NO 2
<211> LENGTH: 23
<212> TYPE: DNA
<213> ORGANISM: Homo sapiens

<400> SEQUENCE: 2
ccctgttaaa aacacacaca cac     23

<210> SEQ ID NO 3
<211> LENGTH: 24
<212> TYPE: DNA
<213> ORGANISM: Homo sapiens

<400> SEQUENCE: 3
tgtaggaagt caccaaagca gtac     24

<210> SEQ ID NO 4
<211> LENGTH: 21
<212> TYPE: DNA
<213> ORGANISM: Homo sapiens

<400> SEQUENCE: 4
cccggataac aaggaggaac a     21

<210> SEQ ID NO 5
<211> LENGTH: 21
<212> TYPE: DNA
<213> ORGANISM: Homo sapiens

<400> SEQUENCE: 5
cccggataac aaggaggaac g     21

<210> SEQ ID NO 6
<211> LENGTH: 19
<212> TYPE: DNA
<213> ORGANISM: Homo sapiens

<400> SEQUENCE: 6
caaccgccaa caactgtcc     19

METHOD FOR LONG RANGE ALLELE-SPECIFIC PCR

CROSS REFERENCE TO RELATED APPLICATION

This application claims the benefit of the filing date of U.S. Provisional Patent Application Ser. No. 60/598,226, filed Aug. 2, 2004, the disclosure of which is incorporated, in its entirety, by this reference.

BACKGROUND OF THE INVENTION

The present invention generally relates to the field of nucleic acid chemistry. More specifically, the invention relates to a method of using PCR amplification to determine haplotypes.

Genetic research has shown that an individual's disease, risk of disease and response to therapeutic treatment is determined by variants or polymorphisms (alleles) in a gene at a particular genetic locus or in some cases at multiple genetic loci. The particular combination of genetic polymorphisms at multiple loci is referred to as the "haplotype". Identification and characterization of such polymorphisms, particularly haplotypes, has therefore become a primary focus of genetic research.

In order to map disease genes and establish founder effects attributable to haplotypes, it is necessary to determine whether or not polymorphisms at multiple genetic loci are present on the same chromosome (the linkage phase). Eukaryotes, such as human, animals and plants, contain two copies of each gene, one on each of two chromosomes inherited from a parent (with the exceptions that the male X and Y chromosomes contain only a single copy of genes, and mitochondrial DNA is present as maternally inherited copies. Frequently, these two copies contain differences in the DNA sequence, attributable to mutations or recombination events, which may increase the risk of or cause a disease, or may render an individual more or less responsive to drug treatment. If a particular mutation in a gene is present on one of the genes but not the other, the gene is said to be heterozygous for that mutation. If both genes have the same mutation, the mutation is homozygous. Certain diseases are manifest only if a gene has multiple mutations at different locations on the same gene (the mutations are in cis phase), while the disease is not manifest if the same mutations are present but on different chromosomes (the mutations are in trans phase). Vice versa, disease can be associated with the trans phase on two mutations while the non-disease status is associated with the cis phase In the event that a gene is determined to have polymorphisms at multiple genetic loci, it is often difficult to determine whether those polymorphisms are present on the same copy of the gene (i.e., the same chromosome). For example, two polymorphisms could be present on one gene (in which case the two markers are said to be in cis phase), or alternatively the two polymorphisms could be present on different chromosomes (in which case the two markers are said to be in trans phase). Thus, if an individual is heterozygous for particular variants, it is necessary to establish whether both mutations are in cis or in trans to correctly analyze the individual's disease risk status and provide adequate genetic counseling.

Although genetic polymorphisms at a single genetic locus can be easily detected using basic PCR techniques, it is significantly more complex to determine the haplotype of a locus having polymorphisms at multiple genetic loci. Traditionally, haplotyping of multiple mutations has been established by analysis of the parental lineage when available or by inference from genotypes in rare cases of homozygocity or known compound heterozygotes. Such methods, however, are costly and time consuming, and are not therefore practical for use in clinical or diagnostic situations.

A number of alternative approaches have been developed to determine the haplotype or linkage phase of a gene (the particular combination of polymorphisms on a gene) using molecular methods. For haplotyping of a gene with multiple polymorphisms located short distances from each other, the typical approach has been to use allele specific amplification by PCR, a relatively easy method that has generally been useful only for analysis of polymorphisms sufficiently close in proximity that the genetic loci of the polymorphisms can be amplified together (typically in the range of 1 kilobase (kb), the practical limit of accurate PCR amplification) (See, e.g., Ruano et al., Nucleic Acids Res. 1989, 17:8392). Allele specific amplification is commonly used in genotyping assays where both alleles are amplified with distinguishable primers and analyzed.

Wu et al. disclose a direct molecular haplotyping method that uses allele-specific enzymatic PCR amplification of the beta-globin genomic DNA to diagnose sickle cell anemia. Two allele-specific oligonucleotides primers, one specific for the sickle cell allele and one specific for the normal allele, together with another primer complementary to both alleles were used in the polymerase chain reaction with genomic DNA templates. The allele-specific primers differed from each other in their terminal 3' nucleotide. PCR amplification was performed under annealing temperatures and polymerase chain reaction conditions that permitted directed amplification on their complementary allele. The authors suggest, however, that the DNA polymerase enzyme used to initiate primer extension cannot possess 3'→5' exonuclease activity, since "such an activity would correct the mismatched base pair in the mismatched primer-template complex and then permit efficient priming with the one-nucleotide-shorter primer". Thus, the allele-specific PCR amplification of Wu et al. is useful for discriminating between two alleles that differ by a single nucleotide, but this method is useful only when the DNA polymerase lacks 3'→5' exonuclease activity, since such an enzyme would otherwise remove the single nucleotide mismatch and allow PCR to proceed with both alleles, thereby negating the discriminatory ability of the assay.

For haplotyping of polymorphisms separated by greater distances on a gene, the most common methods have required physical separation of chromosomes or cloning of individual alleles to identify which mutations are present on which of the two diploid chromosomes. These haplotyping technologies are impractical and cost-prohibitive for clinical applications, and have rarely been applied to clinical testing for several reasons: the methods are labor intensive and highly sophisticated, rely on extreme dilution of DNA not practical in a clinical setting, are limited to short fragments of DNA, or are not accurate enough to determine haplotypes from specific individuals.

Recently, a molecular haplotyping technique has been disclosed that uses a two-step procedure to determine the phase of two distantly located alleles (McDonald et al., Pharmacogenetics 2002, 12:93-99). First, long range PCR is used to amplify the region of the gene containing both polymorphic loci, followed by post PCR intramolecular ligation (circularization) to bring the polymorphisms into close proximity so that PCR amplification can be used to determine whether the polymorphisms reside on the same or different chromosomes. This approach has the disadvantage of requiring additional post-PCR steps prior to analysis, and is susceptible to intermolecular ligation between molecules, which can confound results.

Another method for molecular haplotyping of distantly located genetic markers has been disclosed by Michalatos-Beloin et al. (Nucleic Acids Research 1996, 24:4841-4843). In this method, the haplotype of a bi-allelic Alu deletion and a multi-allelic pentanucleotide short tandem repeat (STR) are separated by 10 kb. Both alleles differ by an Alu insertion, providing a long specific sequence for the allele-specific primer. This method requires significant differences between the different alleles at a particular genetic locus, and is not useful for discriminating between alleles that differ by a single nucleotide.

Inbar et al. (Nucl. Acids Res. 30 (15) e76 (2002) disclose determination of haplotypes of two SNPs, SNP888 and SNP988, in close vicinity, separated by a distance of 7.4 kb in the APOE gene, using the method described by Michalatos-Beloin et al., described above.

Advances in the field of human genome mapping, the search for complex disease determinants, pharmacogenomics and accumulation of data from mutation screening programs emphasize the need to develop efficient and cost-effective methods for direct molecular haplotyping, without relying on family pedigree analysis, cloning or complex instrumentation.

BRIEF DESCRIPTION OF THE INVENTION

The present invention is a method for discriminating between two haplotypes on the basis of a difference of one or more nucleotides using allele-specific PCR amplification with a DNA polymerase enzyme having 3'→5' exonuclease activity. In particular, the present invention is a method of using allele-specific PCR in combination with long range PCR using a DNA polymerase enzyme having 3'→5' exonuclease activity, under annealing temperature conditions sufficiently greater than the predicted annealing temperature (Tm) to effect selective hybridization and extension of an allele-specific extension primer to the target allele relative to the variant allele. The present invention is particularly useful for determining the haplotype of a gene having multi-allelic genetic loci separated by a distance in which accurate PCR amplification of a single fragment containing the multiple genetic loci cannot be performed without using a DNA polymerase enzyme having 3'→5' exonuclease activity, generally about 5 kilobases or more.

In another embodiment, the method of the present invention includes a method for selectively amplifying a polynucleotide segment, wherein the method comprises: preparing a reaction mixture comprising: (i) a heterozygous sample comprising a polynucleotide template having a target allele and a polynucleotide template having a variant allele, wherein the target allele and the variant allele differ by a single nucleotide polymorphism; (ii) an allele-specific extension primer having a sequence complementary at its 3' nucleotide to the target allele; (iii) a common extension primer having a sequence complementary to a remote locus common to both polynucleotide templates of the target allele and the variant allele, and having the opposite orientation relative to the first extension primer; (iv) a dNTP mixture; and (v) a polymerase enzyme having 3'→5' exonuclease activity; and then amplifying the polynucleotide segment under polymerase chain reaction conditions, wherein the annealing temperature is between about 5° C. and about 11° C. greater than the predicted annealing temperature for the allele-specific extension primer and its complementary sequence, thereby selectively effecting hybridization of the first extension primer to the target allele and extension of the primer, relative to the variant allele.

In another aspect, the present invention is a method for determining the molecular haplotype of a gene in a diploid DNA sample, wherein the method comprises preparing a reaction mixture comprising: (i) a diploid DNA sample containing a gene heterozygous at a first locus and at a second locus, wherein the first locus has a target allele and a variant allele that differ by a single nucleotide polymorphism, and the second locus has two alleles that differ by any polymorphism; (ii) an allele-specific extension primer having a sequence complementary at its 3' nucleotide to the target allele of the first locus; (iii) a common extension primer having a sequence complementary to a remote locus common to both polynucleotide templates of the target allele and the variant allele, wherein the common extension prior encompasses the alleles of the second locus and has the opposite orientation relative to the first extension primer; (iv) a dNTP mixture; and (v) a polymerase enzyme having 3'→5' exonuclease activity; and then amplifying the polynucleotide segment under polymerase chain reaction conditions, wherein the annealing temperature is between about 5° C. and about 11° C. greater than the predicted annealing temperature for the allele-specific extension primer and its complementary sequence, thereby selectively effecting hybridization of the first extension primer to the target allele and extension of the primer, relative to the variant allele, and detecting the allele of the second locus in the resulting amplification product.

In another embodiment, the annealing temperature is between about 8° C. and about 11° C. greater than the predicted annealing temperature for the allele-specific extension primer and its complementary sequence.

In another embodiment, the length of the amplified polynucleotide segment is greater than 10 kb.

In another embodiment, the present invention is a method for determining the molecular haplotype of the CFTR gene, wherein the method comprises preparing a reaction mixture comprising: (i) a diploid DNA sample containing the CFTR gene heterozygous at the R117H locus and heterozygous at the IVS-8 polyT locus; (ii) an allele-specific extension primer having a sequence complementary to a region encompassing the R117H locus, and wherein the last 3' nucleotide is complementary to a target allele selected from the 117R and 117H alleles of the R117H locus; (iii) a common extension primer having a sequence complementary to a region common to both alleles of the IVS-8 polyT locus, wherein the common extension primers encompass the IVS-8 polyT locus and have the opposite orientation relative to the allele-specific extension primer; (iv) a dNTP mixture; and (v) a polymerase enzyme having 3'→5' exonuclease activity; and then amplifying the polynucleotide segment under polymerase chain reaction conditions, wherein the annealing temperature is between about 5° C. and about 11° C. greater than the predicted annealing temperature for the allele specific extension primer and its complementary sequence, thereby selectively effecting hybridization of the first extension primer to the target allele and extension of the primer, relative to the variant allele; and detecting the allele of the IVS-8 5T locus in the resulting amplification product.

The present invention also includes a kit for determining the molecular haplotype of a gene in a diploid DNA sample containing a gene heterozygous at a first locus and at a second locus separated by a distance of more than 10 kb, wherein the first locus has a target allele and a variant allele that differ by a single nucleotide polymorphism, and the second locus has two alleles that differ by any polymorphism, wherein the kit comprises: (a) an allele-specific extension primer having a sequence complementary at its 3' nucleotide to the target allele of the first locus; (b) a common extension primer having a sequence complementary to a remote locus common to both polynucleotide templates of the target allele and the variant allele, wherein the common extension primer encompasses the alleles of the second locus and has the opposite orientation relative to the allele-specific extension primer; (c) a dNTP mixture; and (d) a polymerase enzyme having 3'→5' exonuclease activity.

The present invention, and other particular embodiments, are described in more detail below.

BRIEF DESCRIPTION OF THE FIGURES

FIG. 1 illustrates the experimental design of the assay, as applied to the CFTR gene. The 3 PCRs are represented under the map of the relevant section of the CFTR gene. "RH" is the PCR that amplifies both the wild type and the R117H mutant allele. Ralsp and Halsp amplify the wild type allele (R) and the mutant allele (H) respectively. Names of the primers are located next to thick arrows indicating their directions.

FIG. 3 shows the analysis of long range allele specific PCR by OLA and FRET. A and B: OLA analysis. The 3 PCRs from a sample are analyzed in the "green" channel and organized from top to bottom as "RH" then "Haslp", then "Ralsp". The horizontal axis represents fragment size in terms of nucleotide base pairs (bp). The vertical axis indicates fluorescence. The bottom graph in A shows signals detected in the "yellow" channel that correspond to other positions on the 17.7 kb PCR fragment, as described in the examples. C and D show the melting curve analysis of the IVS-8 polymorphisms. Amplification from both alleles ("RH" reaction) are shown with a shaded line, wild type allele-specific are shown with a solid line, and mutant allele-specific is shown with a dashed line. No-template controls for the 3 reactions are also shown as dotted lines at the bottom of the graph.

DETAILED DESCRIPTION OF THE INVENTION

In order that the present invention may be more readily understood, certain terms are first defined. Additional definitions are set forth throughout the detailed description.

Definitions

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

As utilized in accordance with the present disclosure, the following terms, unless otherwise indicated, shall be understood to have the following meanings:

As used herein, a "sample" refers to any substance containing or presumed to contain nucleic acid and includes a sample of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA. The oligonucleotide is comprised of a sequence of approximately at least 6 nucleotides, preferably at least about 10-12 nucleotides, and more preferably at least about 15-25 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The term "gene," as used herein, means a hereditary unit consisting of a sequence of DNA that occupies a specific location on a chromosome and determines a particular characteristic in an organism.

The term "genetic locus," as used herein, means a specific position or specific region on a chromosome. In the context of the present invention, the term genetic locus refers to a particular position or region of polynucleotide sequences of a chromosome with which are associated multiple allelic variants.

The term "remote locus," as used herein, means either a locus which is upstream or downstream from the locus of a particular reference polynucleotide sequence.

The term "encompass," as used herein in reference to the location of a primer relative to a reference genetic locus, means that a PCR extension primer is located so as to amplify the genetic locus. The primer may include nucleotide sequences that correspond or are complementary to all or part of the genetic locus. Alternatively, the primer may be complementary to a region located 3' of the reference genetic locus.

The term "heterozygous," as used herein, means that a particular chromosomal loci has two or more different alleles. With reference to a sample, the term "heterozygous" means that the sample has two copies of a chromosome or polynucleotide sequence that have two or more different alleles at a particular locus.

The term "haplotype," as used herein, means a set of two or more alleles (at different loci) on a single chromosome that are inherited together as a unit, providing a distinctive genetic pattern.

The term "amplification," as used herein means the exponential reproduction of a polynucleotide sequence under conditions of polymerase chain reaction.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains 15-25 nucleotides, although it may contain more or fewer nucleotides. Short primer molecules generally require lower temperatures to form sufficiently stable hybrid complexes with the template.

The term "extension primer," as used herein, means a polynucleotide sequence that is complementary to a template sequence, and which is capable of hybridizing and extending a sequence under polymerase chain reaction conditions.

The term "common primer," as used herein, means a polynucleotide sequence that is complementary to a region that is common to two or more polynucleotide templates.

The term "allele," as used herein, means a particular genetic variant or polymorphism in the sequence of a gene, representing an alternative form of the gene.

The term "target allele" or "target sequence," as used herein, refers to a region of a polynucleotide template sequence that is to be selectively amplified. The target allele resides between the two primer sequences used for amplification. The target allele may represent either a wild-type or consensus sequence, characteristic of the predominant form of the gene, or alternatively may represent a polymorphic variant that is present in a population at a lower frequency.

The term "variant allele" or "variant sequence," as used herein, refers to a region of a polynucleotide template sequence that differs from the target allele by one or more nucleotides, and with respect to which the target allele is being selectively amplified. The variant allele may represent either a wild-type or consensus sequence, or alternatively may represent a polymorphic variant that is present in a population at a lower frequency. Thus, the terms "target allele" and "variant allele" are used arbitrarily to designate one allele and another allele, and are not used to designate or differentiate the frequency of any particular allele in a population.

The term "allele-specific," when used in reference to nucleic acid sequences, such as oligonucleotides and primers, means that the nucleic acid sequence is complementary with the target allele of a reference sequence. As used herein, an "allele-specific" primer is a primer that is exactly complementary to the nucleotides of the target allele that differ from the variant allele. For example, if a target allele and a variant allele differ by a single nucleotide polymorphism, the 3' end of the primer will be exactly complementary to one or the other nucleotide polymorphic variants (which will be the 5' nucleotide of the target allele). While the allele-specific primer is preferably exactly complementary to the target allele with respect to all nucleotides, it is contemplated that the method of the present invention also includes use of allele-specific primers that are exactly complementary at the 3' end of the primer, but are only substantially complementary at other nucleotides positions, such that the allele-specific primer preferentially hybridizes and extends under PCR conditions to the target allele relative to the variant allele.

The term "complement," and its related adjectival form "complementary," when used in reference to two nucleic acid sequences, means that when two nucleic acid sequences are aligned in anti-parallel association (with the 5' end of one sequence paired with the 3' end of the other sequence) the corresponding G and C nucleotide bases of the sequences are paired, and the corresponding A and T nucleotide bases are paired. Certain bases not commonly found in natural nucleic acids may be included in the nucleic acids of the present invention and include, for example, inosine and 7-deazaguanine.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Typically, the primers have exact complementarity to obtain the best detection results.

The term "Tm" means the melting temperature, or annealing temperature, of a nucleic acid duplex at which, under specified conditions, half of the base pairs have disassociated. Those skilled in the art of nucleic acid technology can determine duplex stability empirically considering a number of variables including, for example, the length of the oligonucleotide, base composition and sequence of the oligonucleotide, ionic strength, and incidence of mismatched base pairs. The "predicted Tm," as used herein, means the temperature at which a primer and its complementary template sequence are predicted to be sufficiently stable to permit hybridization and extension by PCR, and is determined using the nearest neighbor algorithm (Von-Ahsen N et al 1999 Clinical Chemistry, 45:12, 2094-2101). A software tool for determining the predicted Tm for oligonucleotides and primers based on the nearest neighbor algorithm is available from, for example, commercial sources such as Integrated DNA Technologies.

As defined herein, "3'→5' exonuclease activity" refers to the activity of a template-specific nucleic acid polymerase having a 3'→5' exonuclease activity associated with some DNA polymerases, in which one or more nucleotides are removed from the 3' end of an oligonucleotide in a sequential manner.

The term "probe," as used herein, refers to a labeled oligonucleotide which forms a duplex structure with a sequence in the target nucleic acid, due to complementarity of at least one sequence in the probe with a sequence in the target region. The probe preferably does not contain a sequence complementary to sequence(s) used to prime the polymerase chain reaction.

The practice of the present invention will employ, unless otherwise indicated, conventional techniques of molecular biology, microbiology, recombinant DNA techniques, oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

The present invention is directed to a method for allele-specific PCR amplification of a polynucleotide sequence to selectively or preferentially amplify a specific polynucleotide segment relative to another polynucleotide segment on the basis of one or more nucleotide differences. More particularly, the present invention is a method for improving the ability of allele-specific PCR to discriminate between two alleles that differ by one or more nucleotides, using allele-specific PCR amplification in combination with a polymerase enzyme having 3'→5' exonuclease proofreading activity. This method is particularly useful, for example, for selectively amplifying a polynucleotide sequence having one of the alleles of a known mutation, resulting in PCR fragment longer than about 5 kb, and more preferably longer than about 10 kb. The discriminatory capability of the method of the present invention is also able to selective amplify polynucleotide sequences longer than about 15, 20, 25 and 30 kb. The use of allele-specific PCR in combination with a polymerase enzyme having 3'→5' exonuclease proofreading activity is enabled by increasing the annealing temperature sufficiently greater than the predicted annealing temperature (Tm) for the extension primer and the complementary template to selectively effect hybridization and extension of the extension primer relative to an extension primer the common.

The present invention is also a method for determining the molecular haplotype (the combination of multiple alleles on a single gene) in a diploid DNA sample by PCR amplification of a region of DNA encompassing the alleles defining the haplotype and detecting which alleles are present on the amplified product. In accordance with this method, a sample containing a polynucleotide template is provided which is known to be heterozygous (i.e., has multiple alleles) at one particular genetic locus, or which is known to be heterozygous at two or more genetic loci. Allele-specific PCR, using a polymerase enzyme having 3'→5' exonuclease proofreading activity, is used to selectively amplify only one of the alleles to the exclusion of the other alleles, on the basis of a nucleotide polymorphism of one or more nucleotides. The present invention is also directed to a method for detecting specific gene mutations, in particular detecting the presence of including determining the haplotype of a gene, by combining the methods of allele-specific PCR and long range PCR, which were previously considered to be incompatible. The method of the present invention allows these two PCR techniques to be used together, by increasing the annealing temperature conditions sufficiently greater than the predicted Tm (annealing or melting temperature) to effect selective hybridization and extension of a target allele relative to the single nucleotide variant allele.

In particular embodiments, the present invention is useful in determining the haplotype (i.e., the particular combination of alleles) of a gene that is heterozygous at two remote genetic loci separated by a large distance by selectively amplifying by PCR a segment DNA that differs from other DNA by a single nucleotide polymorphism, thereby avoiding the need to obtain DNA from parents or relatives. While the present invention is particularly useful for determining the haplotype of gene having polymorphisms at loci separated by long distances, it is not limited to this application, and may also be used to discriminate between alleles of a single genetic loci, or between alleles of multiple genetic loci separated by shorter distances.

The invention described herein is an improved method for allele-specific PCR, which may be used to amplify polynucleotide segments spanning a long range. Allele-specific amplification has so far been restricted to amplification of fragments of DNA less than about 5 kb and that do not require the use of an enzyme with proof reading activity provided by the 3' to 5' exonuclease activity. It is shown here that under optimal PCR conditions allele-specific PCR can be applied to long fragments using long range PCR. These two techniques were previously believed to be incompatible because the proof reading activity of the polymerase used in long range PCR should remove the 3' end allele specific mismatch and allow PCR of both alleles. The reaction has surprising been found to be allele-specific if performed at a temperature higher than predicted for primer annealing and extension. The PCR products produced by the method can be analyzed using hybridization probes added after long range PCR is completed. Analysis of the PCR product may also be done by using other methods of detecting the presence of polymorphisms.

In a particular embodiment, the present invention provides a method of performing long range allele specific PCR using a polymerase with proofreading activity and a single nucleotide polymorphism as a site for the specific primer. In order to haplotype a gene, amplification of the DNA from only one allele is required per reaction and the annealing temperature during PCR must be sufficiently greater than the predicted Tm of the allele-specific extension primer to the complementary template so as to selectively effect hybridization and extension of the allele-specific extension primer to the template relative to the second extension primer, thereby achieving specificity of the reaction. While not wishing to be bound by any particular theory as to the mechanism by which this result is achieved, it is possible that the proofreading activity of the polymerase shortens the mismatched primer by one nucleotide giving the longer matched primer enough thermodynamic advantage to participate in the final product.

PCR Amplification

The present invention is directed to a process for selectively amplifying and discriminating any one or more specific nucleic acid sequences from polymorphic variants of such sequences, using the technique of polymerase chain reaction (or PCR). Polymerase chain reaction (PCR) is very widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

To briefly summarize, in the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

Preparation of Polynucleotide Templates

Any specific nucleic acid sequence can be amplified by the present process. It is only necessary that a sufficient number of bases at both ends of the sequence be known so that two primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge of the bases at both ends of the sequence, the greater can be the specificity of the primers for the target nucleic acid sequence, and thus the greater the efficiency of the process.

Any polynucleotide molecule, in purified or nonpurified form, can be utilized as the starting nucleic acid or acids, provided it contains the sequence being detected. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the beta-globin gene contained in whole human genomic DNA, or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The nucleic acid templates may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi or amniotic cells by a variety of techniques such as that described by Maniatis et al., Molecular Cloning (1982), 280-281. The method of the present invention are particularly useful in analyzing genomic DNA.

The cells may be directly used without purification of the nucleic acid if they are suspended in hypotonic buffer and heated to about 90°-100° C., until cell lysis and dispersion of intracellular components occur, generally about 1 to 15 minutes. After the heating step the amplification reagents may be added directly to the lysed cells. This direct cell detection method may be used on peripheral blood lymphocytes and amniocytes.

The target nucleic acid contained in the sample may be in the form of genomic DNA, or alternatively may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers, and, optionally, a labeled oligonucleotide (referred to herein as a "probe") for purposes of detecting the amplified sequence) under conditions that facilitate the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

In one embodiment, the long range allele-specific PCR amplification method of the present invention is used to selectively amplify a polynucleotide segment of a gene in a sample that has a known polymorphic variant or allele. In this case, the sample material will comprise a polynucleotide template that has both a target allele and a polynucleotide template having a variant allele that differs from the target allele by a single nucleotide polymorphism.

In another embodiment, the long range allele-specific PCR amplification method of the present invention is used to determine the molecular haplotype of a gene in a diploid DNA sample. In this case, the sample comprises diploid DNA having a gene that is heterozygous at a first locus and is also heterozygous at a second locus. The first locus has a target allele and a variant allele that differ by a single nucleotide polymorphism, and the second locus has a target allele and a variant allele that differ by any polymorphism, such as a single nucleotide polymorphism, a deletion polymorphism, addition polymorphism or substitution polymorphism involving any number of nucleotides.

PCR Extension Primers

In the methods of the present invention, PCR amplification is performed using extension primers that span the region encompassing the allele. Extension primers must be sufficiently long to prime the synthesis of extension products in the presence of the agent for polymerization. The exact length and composition of the primer will depend on many factors, including temperature of the annealing reaction, and the source and composition of the primer. For example, depending on the complexity of the target sequence, the oligonucleotide primer typically contains about 15-30 nucleotides, although a primer may contain more or fewer nucleotides. Preferably, primers will contain around 20-25 nucleotides. The primers must be sufficiently complementary to anneal to their respective strands selectively and form stable duplexes.

In the context of the present invention, allele-specific PCR is performed for the purpose of discriminating between two or more alleles of a genetic locus that differ by a single or multiple nucleotide polymorphism. A forward extension primer used will be complementary to one allele, but differ from the other alleles. Specifically, the forward extension primer will have a sequence complementary to a region encompassing the target allele, with the last 3' nucleotide of the forward extension primer being exactly complementary to the target allele, but differing from the variant allele by one or more nucleotide at the 3' terminus of the primer. As a result of the nucleotide mismatch between the 3' terminus of the primer and the 5' initiation point of the template, the exactly matching primer will preferentially hybridize and extend under appropriate PCR conditions over the mismatching primer.

The method of the present invention also contemplates PCR amplification using a reverse extension primer having a sequence complementary to a separate region common to both genes of the target allele and the variant allele, but which is located at a locus remote from the specific genetic locus of the target allele and variant allele. The reverse extension primer will have the opposite orientation relative to the forward extension primer. The forward and reverse extension primers thus define a region of DNA that will be amplified when subjected to PCR amplification conditions. The reverse extension primer is preferably complementary to a polynucleotide sequence that is common to both the gene of the target allele and the gene of the variant allele at a position located downstream (in the 3' direction) from the multi-allelic genetic locus of interest. Preferably, the common extension primer may be specific to a second multi-allelic genetic locus located downstream from the first multi-allelic genetic locus.

The allele-specific primers used in the method of the present invention are exactly complementary to the target sequence. The non-specific primers used for PCR amplification are generally selected to be substantially complementary to the different strands of each specific sequence to be amplified. The primers need not reflect the exact sequence of the template, but must be sufficiently complementary to hybridize selectively to their respective strands. Non-complementary bases or longer sequences can be interspersed into the primer or located at the 5' end of the primer, provided the primer retains sufficient complementarity with a template strand to form a stable duplex therewith.

Although the methods of the present invention may be used to amplify a polynucleotide sequence of any length, the methods are particularly advantageous for use in amplifying polynucleotide sequences having a length greater than standard PCR amplification is able to accurately amplify a template sequence with high fidelity. Accordingly, in one particular embodiment, the present invention is used to amplify a polynucleotide sequence of more than about 5 kilobases, more than about 10 kilobases, more than 20 kilobases, or more than 40 kilobases.

Allele-Specific PCR Amplification

The present invention contemplates use of the PCR-based method for determining the presence or absence of a specific known nucleic acid sequence, such as a mutation (e.g. a genetic polymorphism), called allele-specific PCR (ASP) or allele-specific amplification (ASA), also known as amplification refractory mutation system (ARMS) and PCR amplification of specific alleles (PASA), as described in U.S. Pat. No. 5,639,611; Ruano et al., Nucleic Acids Res 17:8392 (1989) (allele-specific amplification), Ruano et al., Nucleic Acids Res. 19:5887-5882 (1991) (coupled amplification and sequencing) and Cheng et al., Nature 368:664-665 (1994). Allele-specific PCR amplification (ASA) is used to selectively amplify one specific predetermined allele from a sample containing multiple alleles at the same genetic locus.

In a typical ASP assay one or more PCR reactions using different PCR extension primers are annealed to the same nucleic acid sample. The PCR primers are designed to have a residue at the 3'-terminus of the primer (complementary to the 5' primer initiation site of the template) that is complementary to one of the two allelic variants and not to the other. The PCR reaction does not extend from a primer having a 3'-terminal mismatched base, unless the polymerase used has a 3'→5' proofreading activity that removes the mismatched base and inserts the correct base. Proofreading repairs the PCR primer and destroys the extension discrimination between the two alleles. Therefore, a polymerase lacking 3'→5' proofreading activity, such as Taq DNA polymerase has traditionally been used in an ASP assay.

Although discrimination between specificity of PCR extension from the allele-specific ASP primers is known to be enhanced by the introduction of deliberate multiple mismatches near the 3'-terminal nucleotide, this significantly reduces the overall PCR extension product yield. See, e.g., Ruano et al., Nucleic Acids Res. 17:8392 (1989). Other factors known to affect the stability of the hybridization of PCR primers in an ARMS assay include the position of additional mismatches in the primer, the GC content of the 5 or 6 nucleotides preceding the 3' nucleotide, and the discriminatory 3'-terminal nucleotide, depending on the difference between the alleles and the type of mismatch. The destabilization is greater when the second mismatch is nearer to the 3'-terminal nucleotide. The destabilizing effect of additional mismatches on ASP has been ranked qualitatively (CC>CT>GG=AA=AC>GT). In contrast, the method of the present invention has been shown to be effective in discriminating on the basis of a single nucleotide mismatch when performed under appropriate PCR amplification conditions, as described below.

In the present invention, a polynucleotide segment is selectively amplified from a heterozygous sample comprising a polynucleotide template having a target allele and a polynucleotide template having a variant allele. The target allele and the variant allele differ by one or more nucleotides. An allele-specific extension primer having a sequence complementary at its 3' nucleotide to the target allele is used, together with a common extension primer having a sequence complementary to a remote locus common to both polynucleotide templates of the target allele and the variant allele, and having the opposite orientation relative to the first extension primer. The primers are combined with a dNTP mixture and a polymerase enzyme having 3'→5' exonuclease activity, and the polynucleotide segment is amplified under polymerase chain reaction conditions, wherein the annealing temperature is between about 5° C. and about 11° C. greater than the predicted annealing temperature for the allele-specific extension primer and its complementary sequence, thereby selectively effecting hybridization of the allele-specific extension primer to the target allele and extension of the primer, relative to the variant allele.

In an alternative embodiment, the method of the present invention is used to determine the molecular haplotype of a gene in a diploid DNA sample. In this embodiment, a reaction mixture is prepared comprising: (i) a diploid DNA sample containing a gene heterozygous at a first locus and at a second locus, wherein the first locus has a target allele and a variant allele that differ by a single nucleotide polymorphism, and the second locus has two alleles that differ by any polymorphism; (ii) an allele-specific extension primer having a sequence complementary at its 3' nucleotide to the target allele; (iii) a common extension primer having a sequence complementary to a remote locus common to both alleles of the second locus, wherein the common extension prior encompasses the alleles of the second locus and has the opposite orientation relative to the first extension primer; (iv) a dNTP mixture; and (v) a polymerase enzyme having 3'→5' exonuclease activity. The polynucleotide segment defined by the allele-specific extension primer and the common extension primer is amplified under polymerase chain reaction conditions, wherein the annealing temperature is between about 5° C. and about 11° C. greater than the predicted annealing temperature for the allele-specific extension primer and its complementary sequence, thereby selectively effecting hybridization of the first extension primer to the target allele and extension of the primer, relative to the variant allele. The allele of the second locus is then detected in the resulting amplification product. This method can be used for determining haplotypes consisting of two or more polymorphisms. The polymorphisms may be any combination of SNPs or polymorphisms that can be genotyped quantitatively, such as microsatellite, insertion or deletion polymorphisms.

Long Range Allele-Specific PCR

The methods of the present invention are particularly advantageous for use in amplifying larger regions of a polynucleotide that require use of a polymerase enzyme with high fidelity having 3'→5' exonuclease activity. Polymerase enzymes having high fidelity 3'→5' exonuclease activity are required, for example, when primer extension must be performed over long distances (i.e., when the desired PCR amplification product is greater than about 5 kb). Exemplary methods for performing long range PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. Efficient long PCR is accomplished using a combination of polymerases, one of which having 3'→5' exonuclease activity, which assures high fidelity generation of the PCR product from the DNA template. Typically, a non-proofreading polymerase, which is the main polymerase in the reaction, is also used in conjunction with the proofreading polymerase. Long range PCR can also be performed using kits, such as LA PCR kit available from Takara Bio Inc.

Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs).

PCR Conditions

The long range allele-specific amplification method of the present invention is performed under standard conditions used for long range PCR, but using modified annealing temperature conditions, as described below. As discussed above, long range PCR is typically performed under annealing temperature conditions approximately the same as the predicted Tm for the extension primer and its complementary template sequence. The predicted Tm is calculated using standard algorithms, such as the nearest neighbor algorithm (Von-Ahsen et al., Clinical Chemistry 45(12):2094-2101 (1999), which is available for Tm determination of oligonucleotides at from Integrated DNA Technologies. Use of the predicted annealing temperature of the extension primer and its complementary template sequence in the long range allele-specific PCR amplification method, however, results in hybridization and extension of the extension primer to both alleles, and does not therefore discriminate between the two alleles. In accordance with the present invention, it has been determined that by increasing the annealing temperature sufficiently greater than the predicted Tm of the extension primer to its complementary template sequence, the extension primer will selectively hybridize to the complementary template sequence and extend to produce a PCR amplification product corresponding to one allele, but not the mismatched allele. Specifically, the annealing temperature conditions are between about 5° C. and about 11° C. greater than the predicted annealing temperature for the forward extension primer and its complementary sequence. More preferably, the annealing temperature conditions are between about 6° C. and about 11° C. greater than the predicted annealing temperature for the forward extension primer and its complementary sequence. More preferably, the annealing temperature conditions are about 7° C. to about 11° C. greater than the predicted annealing temperature for the forward extension primer and its complementary sequence. The annealing temperature conditions may also be from about 8° C. to about 11° C. greater than the predicted annealing temperature for the forward extension primer and its complementary sequence. By using the higher annealing temperatures in accordance with the present invention, allele-specific PCR amplification can be used in conjunction with an enzyme having 3'→5' exonuclease proofreading activity. The upper end of the above ranges (11° C. greater than the predicted annealing temperature) is equivalent to and determined by reference to the maximum annealing temperature of about 68° C. for long-range PCR.

Detection of PCR Amplification Products

Following generation of a PCR amplification product, it is necessary to detect which particular allele or haplotype has been amplified. Any mutation or polymorphism detection system can be used on the long PCR product to detect the mutation (or mutations) associated with the allele specifically amplified on that product. Examples of suitable detection methods include, but are not limited to, oligonucleotide ligation assay (Celera), single nucleotide extension (Orchid), melting of fluorescent probes (Roche, Epoch), hybridization blots (Innova, Roche), oligonucleotide microarray on various support (Nanogen, Luminex, Motorola), pyrosequencing, DNA sequencing, and invader technology (Third Wave). Many other methods are know to those in the art that can be used for detecting PCR amplification products produced in accordance with the present invention.

In detecting PCR amplification products, each allele can be analyzed independently. For example, only the "disease related" allele can be specifically amplified and its haplotype determined. For haplotyping determination, the minimal analysis required is the determination of the locus that was specifically amplified by the long range allele-specific PCR step.

Applications of Long Range Allele-Specific PCR

The long range allele-specific PCR method of the present invention may be used to selectively amplify a polynucleotide sequence of any gene derived from any prokaryotic or eukaryotic organism, including, but not limited to, plants or animals, in particular humans. The method of the present invention is particularly useful for haplotyping genes derived from a diploid organisms (which have two copies of each gene, one copy inherited from each parent). Long range allele-specific PCR is particularly useful in the field of human genetics (to identify the genetic determinants of complex diseases), anthropology (to identify haplotypes associated with particular populations and thereby determination the origin and migration patters of human populations). The invention can be used in the field of human genetics and molecular anthropology because it allows determination of associations of two or more different haplotype blocks marked by their tagged SNPs. These blocks have a length of 20 kb in average and were determined by the human HapMap project. The length of 50 kb allowed by long range PCR combined with allele-specific amplification from one polymorphism in one of the blocks as described in this invention permits analysis of the association of several haplotype blocks.

The present invention is also useful in the field of molecular diagnostics (for determination of haplotype (cis/trans status) of two or more mutations/polymorphism in diseases, such as Cystic Fibrosis gene (CFTR), and Estrogene receptor (ESR1), pharmacogenomics & pharmacogenetics (for determination of an individual's haplotypes in response to drug treatment), cancer genetics (for detection of haplotypes of oncogenes or a tumor suppressor genes, such as p53 haplotypes, or ESR1 haplotypes), infectious disease (for identification of related organisms that differs by polymorphisms kilobases apart). The method of the present invention is especially useful for haplotyping any 2 mutations (or polymorphisms) in cis or trans separated by more than 5 Kb, where one is a single nucleotide polymorphism, and the other is a SNP or other polymorphism (a repeat, small insertion, small deletion, etc.), where such mutations (polymorphisms) are causative (as in the case of Cystic Fibrosis) or where the mutations are markers of specific haplotypes (as in the case of ESR1).

Because the average size of human gene is around 30 Kb, a gene will in general span at least two haploblocks and some mutations in a given gene are not likely to be in linkage disequilibrium. In order to determine directly the association of two or more mutations (or polymorphisms) within one gene a method that can examine kilobases of DNA is required. The present invention allows the determination of haplotypes for the majority of genes with known polymorphisms.

The present invention also permits analysis of disease severity or susceptibility to disease, which may be linked to different haplotypes. For example, the present invention may be used to determine the cis-trans status of the R117H and the IVS-8 T polymorphism in CFTR, as described by Pont-Kingdon et al., J. Mol. Diag. 6 (3), 264-70 (2003).

The present invention may also be used to haplotype the estrogen receptor gene ESR1. Haplotypes created by different association of three polymorphisms found in the ESR1 gene are being studied in relation to osteoporosis, cancer risk and cardiovascular disease. Unlike the CF situation described above, the 3 polymorphisms are markers and not causative. The three polymorphisms are a (TA)n repeat in the promoter of the gene, and two single nucleotide polymorphisms in intron 1: a T to C (Pvu II polymorphism) and an A to G (Xba I polymorphism). The promoter polymorphism is separated by 35 kb from the 2 SNPs of intron 1. Long-Range Allele Specific may be used to establish the haplotypes found in a particular individual. Studies have shown that three of the four possible haplotypes using the Pvu II and the Xba I polymorphisms are found in the overall population. Each of these haplotypes is associated with variable length of the TA repeat. Repeat length have been classified by others as L (fewer than 18 repeats) or H (larger than 18 repeats). To establish the haplotype of the 3 polymorphisms, long-range allele specific PCR can use a common forward primer downstream of the TA repeats site and reverse primers specific for the Xba I polymorphism. The length of the TA would be determined on the allele specific products using a second PCR with a FAM labeled forward primer as described in van Meurs et al., Hum Mol Genet 12:1745-54 (2003). On the same allele specific product, the Pvu II polymorphism can be determined using any genotyping techniques (sequencing, allele specific fluorescent probes, etc.). The proposed primers for are: ccaatgctcatcccaactcc (for the G allele) and ccaatgct-catcccaactct (for the A allele). Predicted Tm for primers is calculated using the "Integrated DNA Technology" oligo-analyser 3.0. The G allele specific primer have a predicted Tm of 56.0° C. when perfectly matched. The A allele specific primer have a predicted Tm of 54.9° C. with the perfectly matched allele. After 3' exonuclease digestion by the polymerase used in long range PCR, the primers Tm would be 53.5° C. The lesser difference of Tm (A allele) is 1.4° C. and should be sufficient to allow specific amplification if PCR is performed at temperature between 60-65° C. (5-10° C. higher than the lowest perfectly matched primer's Tm (54.9° C.).

Other examples include genes where the existence of simple (1 mutation), compound (2 mutations on separate chromosomes) and complex (with two or more mutations on one chromosome and a mutation in the other) genotypes have been reported, for example, MCAD, MTHFR (Tonetti et al., J Inherit Metab Dis. 24:833-42 (2001), HFE (Mullighan et al., Gut 42:566-9 (1998)).

The present invention is also useful in the field of pharmacogenetics, for use in correlating specific individual genetic polymorphisms and individual responses to specific pharmaceutical compound. Examples of haplotypes that are relevant to the field of pharmacogenetics are (but are not limited to) CYP3A4, TPMT, IL4RA (McDonald et al., Pharmacogenetics 12:93-9 (2002).

The present invention is also useful for haplotyping of oncogenes or tumor suppressor genes, which may be associated with cancer susceptibility. Currently, haplotypes in populations are determined using statistical methods. Molecular methods using long-range allele specific could be developed to directly access some of the haplotypes from genes such as BRCA1 and BRCA2, RAD51, TP53 (Bonnen et al., Genome Res 12:1846-53 (2002)), and ESR1 (Weiderpass et al., Carcinogenesis 21:623-7 (2000)).

Example 1

CFTR Haplotyping

The method of the present invention has been shown to be useful for direct molecular haplotyping of the R117H mutation of exon 4 and the 5T polymorphism of intron 8 of the CFTR gene. Both the R117H mutation and the IVS-8 5T variant have been found at a higher frequency in individuals affected with classic or atypical cystic fibrosis. Using the method of the present invention, rapid and accurate direct molecular haplotyping can be performed to assess individuals undergoing CF carrier screening, diagnostic confirmation of affected individuals and molecular testing of patients with atypical CF. If an individual is found to have the R117H mutation and the IVS-8 5T polymorphism, the molecular test can establish the cis/trans status of both mutations without the need to obtain DNA from parents.

The Cystic Fibrosis Transmembrane Regulator (CFTR) gene encodes a chloride channel, and mutations in this gene are responsible for classic cystic fibrosis and atypical forms of the disease. Two of these mutations, R177H in exon 4 and the 5T polymorphism of the polythymidine tract in intron 8 (IVS-8 T polymorphism) have a phenotypic synergic effect, and are separated by a distance of 17.7 kb. The mutation R117H which accounts for approximately 0.8% of mutant alleles, changes an arginine to an histidine in a transmembrane domain of the protein, altering the conductance of the ion channel. The IVS-8 polymorphism affects the splicing efficiency of intron 8. A tract of 7 or 9 T at the 3' end of intron 8 insures proper splicing of the intron while a 5T results in a majority of mRNA lacking exon 9. Each of the mutations is independently considered mild because in both cases, residual activity of the ion channel remains. Therefore, an individual carrying the R117H mutation and the IVS-8 5T polymorphism on two different chromosomes (in trans) is not affected by, nor considered a carrier of classic CF. In contrast, a gene with both R117H and IVS-8 5T (in cis) is severely affected. If an individual is heterozygous for both R117H and the IVS-8 5T variant, it is necessary to establish if both mutations are in cis or in trans to correctly analyze the individual's CF status and provide adequate genetic counseling. Current technologies determine the status of both loci independently, and therefore do not provide information on the phase of both mutations. Haplotyping of these two mutations is established by study of the parental lineage when available or inferred from genotypes in rare cases of homozygocity or known compound heterozygotes. To analyze these cases directly, the method of the present invention is used to conduct a molecular test that haplotypes the mutations, bypassing the need to obtain DNA from parents or relatives. Since the R117H and IVS-8 loci are separated by 17.7 kilobases, directly molecular haplotyping must be based on long-range-allele-specific PCR. Allele specific amplification has so far been restricted to amplification of fragments of DNA less than about 2 kb and that do not require the use of an enzyme with proof reading activity. Under optimal PCR conditions, the technique of allele-specific PCR can be applied to long fragments using long range PCR methods. These two techniques have previously been considered incompatible because the proof reading activity of the polymerase used in long range PCR was expected to remove the 3' end allele specific mismatch and allow PCR amplification of both alleles. In accordance with the present invention, it has been discovered that the reaction may be allele-specific if performed at a temperature higher than predicted for primer annealing. Additionally, the 17.7 kb PCR products are analyzed using hybridization probes added after Long Range PCR is completed. Analysis of the PCR product is also done by using the OLA CF version3.

Analysis of the CF haplotype, two detection methods (OLA and FRET probe) were used, both of which are accurate; however, the OLA method has the advantage of revealing both loci simultaneously. The analysis of the R117H loci from each PCR provides an internal control, and allows one to avoid a possible false interpretation due to accidental switching of tubes. An additional probe set, distinguishing the R117H mutation from the wild type, could also be added to the FRET probe assay and multiplexed with the IVS-8 probe. Another advantage of the OLA is the ability to address other loci in the amplicon, therefore examining additional association of mutations to an haplotype. Of peculiar interest is the analysis of the (TG) tract found adjacent to the T-tract in IVS-8. Length polymorphism of the TG sequence is reported to influence splicing efficiency of intron 8 which might explain the partial penetrance of the 5T tract. Detection systems other than the two described in this publication can also be used to analyze the long range PCR products. The demonstration of the compatibility between long range and allele specific PCR provides an easy approach to molecular haplotyping of other target genes. Since long range PCR can synthesize fragments up to 40 kb, multiple loci can be analyzed on these long fragments of DNA, identifying defined haplotypes. As the average size of haplotype blocks in the human genome in less than 20 kb, long range allele specific PCR can be designed to study specific blocks.

Genomic samples previously genotyped as R117H heterozygous were selected for the development of this assay, and de-identified following IRB protocol. DNA samples were extracted from whole blood on the MagNA Pure LC instrument (Roche Applied Science) with the MagNA Pure LC DNA Isolation Kit I (Roche Applied Science).

Long Range Allele Specific PCR was performed as follows. All reactions are performed in 25 uL final volume using the LA POR kit, ver.2.1. (Takara Mirus Bio Corporation). Reactions contain 1×LA POR buffer II (with 2.5 mM MgCl2 final), 400 uM each dNTP ("dNTP mixture"), 200 nM of each primer, 1.25 units of TaKaRa LA Taq™ and 50 to 100 ng of genomic DNA. Desalted primers were synthesized by the DNA-peptide core facility at the University of Utah. Primers sequences and their predicted Tms were determined using the web-based primer design tool available from Integrated DNA Technologies using the default setting of 250 nM primer concentration and 50 mM monovalent salt) are presented in the Results section. Reactions were performed on a Gene-Amp PCR System 9700 instrument (Applied Biosystems) using the 9600 ramp mode. The cycling parameters are listed in Table 1, which included modified increments of elongation time at each cycle.

TABLE 1

| | Cycling parameters | | | | | | | |
|---|---|---|---|---|---|---|---|---|
| | Hold | | 10 Cycles | | 25 Cycles | | Hold | |
| Steps: | Temp. | Time | Temp. | Time | Temp. | Time | Temp. | Time |
| Denaturation | 92° C. | 2 min | 92° C. | 10 sec | 92° C. | 15 sec | | |
| Annealing | | | 66.8° C. | 30 sec | 66.8° C. | 30 sec | | |
| Elongation | | | 68° C. | 15 min | 68° C. | 15 min* | 68.0° C. | 7 min |

*each cycle increases by 20 seconds.

Following amplification, the R117H and IVS-8 Haplotypes were determined using Oligonucleotide Ligation Assay (OLA). At the end of the PCR, products are analyzed using the Cystic Fibrosis Assay version 3.0 (Celera Diagnostics). This assay is an Oligo Ligation Assay (OLA), substantially as described by Baron et al., Nat. Biotechnol. 14:1279-1282 (1996). In OLA, polymorphic sites are detected by using a set of 3 oligonucleotides. One is common and hybridizes with both alleles. The two others hybridize specifically to one allele or the other. These allele-specific oligonucleotides have 5' modifier tails of different lengths. After hybridization, the common oligonucleotide is ligated with the immediately adjacent specific oligonucleotide producing allele-specific ligation products. No ligation occurs if there is a mismatch at the 3' end of the allele specific oligonucleotide. Ligation products are analyzed by size. The Cystic Fibrosis Assay version 3.0 from Celera provides all reagents and primers to amplify and analyze 25 CF mutations in addition to the IVS-8 polymorphism following the suggested recommendations of Grody et al., Genet. Med. 3:149-154 (2001). This assay was used for detection only and not for amplification. The R117H and the IVS-8 polymorphism are analyzed concurrently using as template 1.5 uL of the 17.7 kb PCR product previously diluted with 3.5 uL of "diluent for purified DNA" buffer. Oligonucleotide ligation is performed following the manufacturer protocol by adding 5 uL of "OLA mix" containing CF OLA reagent v3 ASR and rTth DNA ligase (P/N 4338109 and P/N 4338114 respectively, Celera Diagnostics) and 0.5 uL of CF v3 5/7/9T OLA ASR (P/N4338111). Products of the ligation reactions are run on the ABI Prism 3100 DNA sequencer instrument (Applied Biosystems) and analyzed using CF Genotyper version 3 from ABI. The R117H and the IVS-8 loci are analyzed in the green channel. Other mutation sites can be examined in the yellow channel.

The R117H and IVS-8 1-Haplotypes were independently determined using hybridization probes. As a confirmatory detection method, we developed fluorescent resonance energy transfer (FRET) hybridization probes to analyze the IVS-8 locus by derivative melting curve analysis on the LightCycler instrument (Roche Applied Science). The IVS-8 polymorphism is detected in the F2 channel using probes designed from GenBank sequence #M55114; 5'-CTATTGT-TATTGTTTTGTTTTGCTTTCT-CAAATAAATTCCCCAAA-LCRed640-3') (SEQ ID NO: 1) and 5'FAM-CCCTGTT AAAAACACACACACAC-phosphate-3') (SEQ ID NO: 2). The probe is an exact match with the 5T allele (underlined). FRET probes were synthesized at Idaho Technology (Salt Lake City, Utah). At the end of PCR, 8 uL of allele specific long range products are mixed with 1 uL of each FRET probe at 2.4 uM (final concentration of each probe is 0.2 uM in 12 µL final reaction) in a capillary tube. The melting cycle profile is as follows: reaction mixtures are denatured 5 minutes at 95° C. and cooled to 40° C. for 2 minutes. Temperature is then increased to 70° C. with a transition rate of 0.1° C./Sec. Fluorescence is monitored continuously during this melting phase. Derivative melting curves distinguish between the 5T, 7T and 9T alleles based on melting temperatures (Tm).

Figure 1:
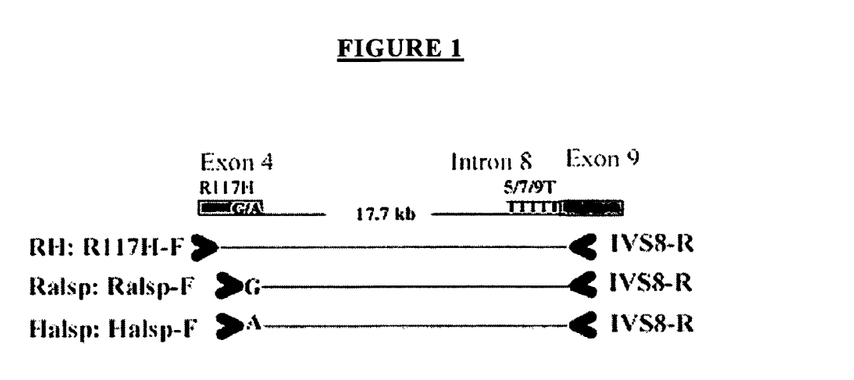
Figure 2:
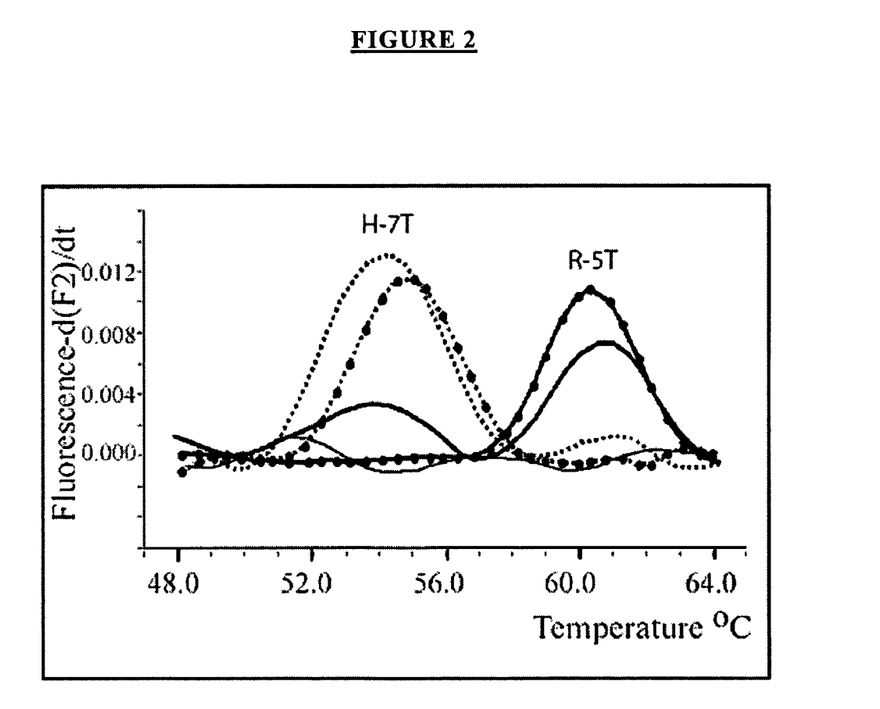
FIG. 2 shows the effect of annealing temperature on specificity of long range allele specific PCR. Derivative melting curves of the IVS-8 locus obtained from the melting profile of allele specific long range PCR products with FRET probes. The curves centered on 54° C. indicate a 7T allele. The curves centered on 61° C. indicate a 5T allele. Reactions performed with an annealing temperature at 60.2° C. are shown with lines (······), (----), and (-). Reactions performed with an annealing temperature at 66.8° C. are shown with lines (··●··●··) and (-●-●-). The "Halsp" reaction is represented with the (······) and (··●··●··) lines, and the "Ralsp" reaction is represented with the (-) and (-●-●-) lines.

Three independent long range PCRs are performed per sample: One reaction amplifies both R117H alleles of the heterozygous R117H sample, while the other two are specific for one allele or the other (FIG. 1). Primer sequences are shown in Table 2. The three PCRs use a common reverse primer (IVS8-R, in exon 9), but three different forward primers. The forward primer of the "RH" PCR (R117H-F) anneals in exon 4, 5' of the mutation site. The allele specific forward primers (Ralsp-F and Halsp-F) differ at the 3' end by the mutation specific nucleotide. This assay differs from allele specific PCRs in which both alleles are amplified in a single reaction with differently labeled primers. Here, only one of the alleles is amplified per allele specific reaction. Long range PCR requires a polymerase with high fidelity. This property is provided by the 3' to 5' exonuclease activity of the enzyme. This activity is presumed incompatible with allele specific amplification because the mismatched nucleotide is removed by the enzyme's proof reading activity. Several different polymerases with proofreading activity and ability to amplify long fragments were tested. Although allele specific amplification of the 17.7 Kb was observed with several kits, reproducible PCR products were observed only with the TaKaRa LA Taq enzyme. As shown in FIG. 2, it was found that the reaction specificity for one allele is improved by higher temperature. The sample shown in FIG. 2 is heterozygous for the R117H mutation and carries the 5T /7T IVS-8 polymorphisms. The FRET probe set that detects the IVS-8 locus dissociates from a 5T allele at 60° C., a 7T allele at 54° C. and a 9T allele at 49° C. When primer annealing is performed at 60.2° C. during the long range PCR, two derivative melting curves are detected (plain curves) indicating amplification from both alleles. When the annealing temperature is increased to 66.8° C., (dotted curves), only the allele specific to the primer is amplified. Table 2 below details the predicted Tms for each primer.

TABLE 2

Primers Sequences

| PCR | Primer | Sequence | Predicted Tm (° C.) R allele | H allele |
|---|---|---|---|---|
| "RH" | R117H-F | 5'-TGTAGGAAGTCACCA AAGCAGTAC (SEQ ID NO: 3) | 58.2 | 58.2 |
| "Halsp" | Halsp-F | 5'-CCCGGATAACAAGGA GGAACA (SEQ ID NO: 4) | 55.8 (1.9) | <u>57.7</u> |
| "Ralsp" | Ralsp-F | 5'-CCCGGATAACAAGGA GGAACG (SEQ ID NO: 5) | <u>58.1</u> | 55.8 (2.3) |
|  | IVS8-R | 5'-CAACCGCCAACAACT GTCC (SEQ ID NO: 6) | 57.7 | 57.7 |

Bold characters indicate the allele-specific nucleotide
Underlined numbers indicate the predicted Tm of the allele-specific primer with the perfectly matched allele.
Delta Tms between perfectly matched and mismatched primer/allele pairs are indicated in parenthesis The optimal annealing temperature for allele-specific amplification is approximately 9° C. higher than the predicted Tms of the perfectly matched allele-specific primers, and approximately 11° C. higher than predicted Tm for the non-specific primer. At this high temperature, amplification from the mismatched primer, presumably shortened by 1 nucleotide by the enzyme proof reading activity and less stable (delta Tms around 2° C., Table 2), is minimum. The minimum temperature still capable of effectively annealing and extending the primer is about 65° C. for the H allele (7° C. higher than the predicted Tm) and 63° C. for R allele (5° C. higher than the predicted Tm).

The R117H samples were haplotypes as follows. Sixteen samples with a variety of IVS-8 genotypes were haplotyped as shown in Table 3 below.

TABLE 3

Genotypes and haplotypes of R117H samples

|  |  | Haplotype | | |
|---|---|---|---|---|
| name | genotype | R chromosome (wild type) | H chromosome (mutant) | Interpretation |
| 5T pos#1 | R117H- 5T/7T | R-5T | H-7T | Trans |
| 5T pos#2 | R117H- 5T/7T | R-7T | H-5T | Cis |
| 5T pos#3 | R117H- 5T/9T | R-9T | H-5T | Cis |
| 5T pos#4 | R117H- 5T/7T | R-5T | H-7T | Trans |
| 5T neg#1 | R117H- 7T/7T | failed | H-7T | na |
| 5T neg#2 | R117H- 7T/7T | R-7T | H-7T | na |
| 5T neg#3 | R117H- 7T/9T | R-9T | H-7T | na |
| 5T neg#4 | R117H- 7T/7T | R-7T | H-7T | na |
| 5T neg#5 | R117H- 7T/7T | failed | H-7T | na |
| 5T neg#6 | R117H- 7T/7T | R-7T | H-7T | na |
| 5T neg#7 | R117H- 7T/7T | R-7T | H-7T | na |
| 5T neg#8 | R117H- 7T/7T | R-7T | H-7T | na |
| 5T neg#9 | R117H- 7T/9T | R-9T | H-7T | na |
| 5T neg#10 | R117H- 7T/9T | R-9T | H-7T | na |
| 5T neg#11 | F508/R117H- 7T/9T | R-9T | H-7T | na |
| 5T neg#12 | G542X/R117H- 7T/9T | R-9T | H-7T | na | na: not applicable

Figure 3:
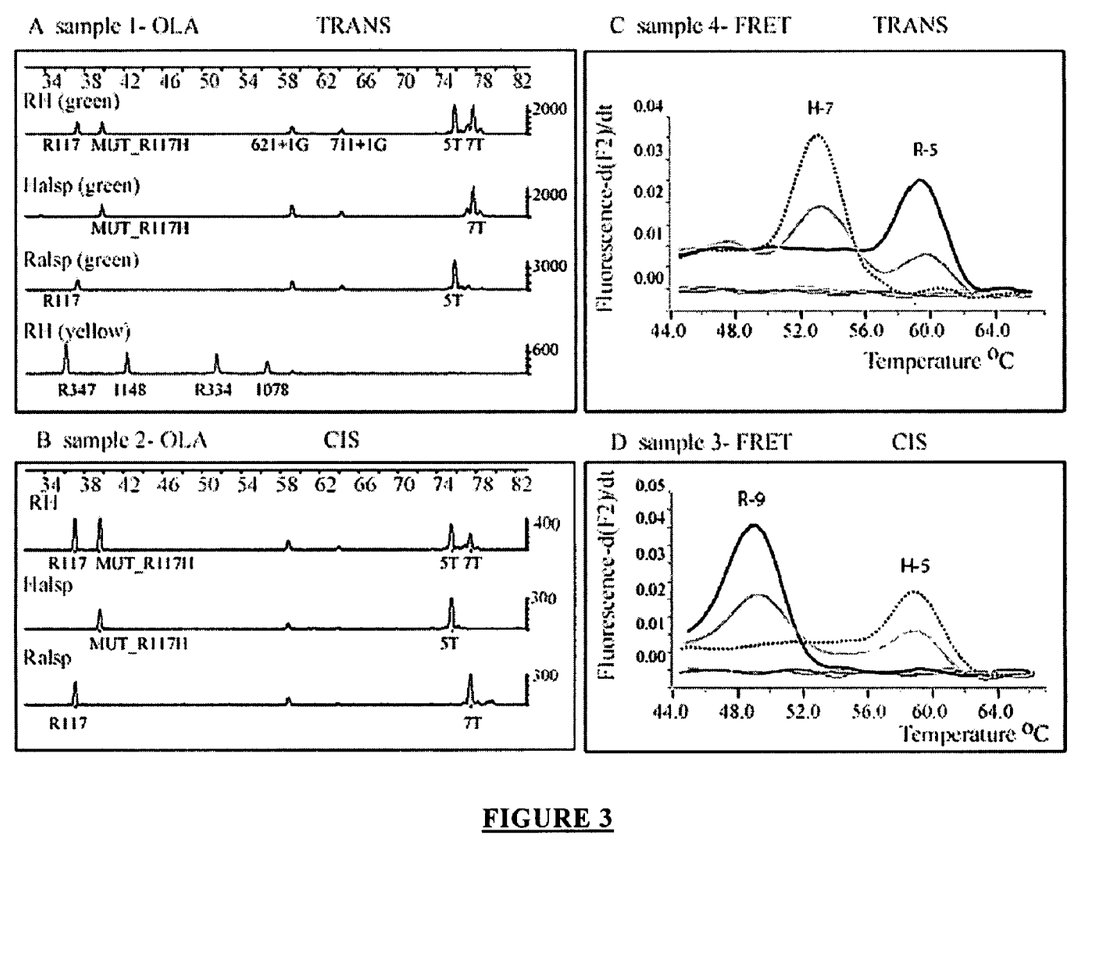

Three samples were heterozygous 5T/7T, one was 5T/9T, five were 7T/9T and seven were homozygous 7T. The 4 samples with a 5T allele were haplotyped with both detection systems (OLA and FRET probes). FIG. 3 shows OLA (A and B) and FRET (C and D) analysis of selected samples. In addition to the R117H and IVS-8 loci, the OLA analysis reveals results for other CF mutation loci included in the CF version 3.0 kit from Celera. In the same channel as R117H and IVS-8, the two extra peaks correspond to the wild type alleles of the 621+1G and 711+G mutations. In the yellow channel, the following loci can be examined: R347, I148, R334, and 1078. This is expected, since all these sites are found in the 17.7 kb amplified fragment. In the sample shown in FIG. 3A all these loci are wild type. Mutations at these positions (621+G>T, 711+1G>T, R347P, I148T, R334W and 1078delT) could be detected and associated with one of the haplotypes. In this analysis, the sample shown in A and C (sample 1) carries the 5T allele on the wild type chromosome (R117) therefore R117H and 5T are in trans. In sample 2 (B) and sample 3 (D), both mutations are in cis. Therefore these two individuals are carriers of a severe mutation in the CFTR gene. Results from all samples are summarized in Table 3, above. Five of the six possible allelic combinations were found in these samples. In the six samples with a 9T allele, this polymorphism is on the wild type chromosome. Genotypes of R117/R117H locus and the 5T/7T/9T locus were confirmed by sequencing the extremities of each PCR obtained from sample 1 and 2. Additionally the haplotype of the Coriell cell line control (GM 13591) was established as R117H-5T (Bemacki et al, submitted).

The method haplotyping method described above was shown to be both accurate and reproducible. Several methods are available for genotyping independently both R117H and IVS-8, but determination of the phase relies on family studies or unequivocal results such as homozygocity of the IVS-8 genotype or compound heterozygous with delF508-9T. Although R117H and the 5T IVS-8 polymorphism are found at relatively high frequency in population affected with CF or with atypical CF, they are relatively rare in the normal population and we found only 4 R117H/5T positive samples in more than 10.000 CF screening tests. In only 1 case, analysis of parental DNA was possible and confirmed the molecular haplotyping data. The molecular assay, analyzed by OLA determined the haplotype of one sample to be R-5T, H-7T. The parent carrying the R117H mutation is IVS-8-7T homozygous and the other parent has the 5T allele (data not shown). Thus, this linkage study confirms the molecular diagnosis that R117H and 5T are in trans in this sample. Specificity of the reaction to one allele is controlled by the PCR conditions and we tested within- and between-run reproducibility of the PCR. Within-run comparison was estimated by setting a triplicate PCR of 2 samples with a 5T allele. Haplotypes, analyzed by OLA provided identical results (data not shown). Additionally, four to five independent PCRs were performed on 3 samples and gave identical data. This suggests that the results (and thus the haplotypes) are not artifacts from the allele specific amplification reaction.

We claim:

1. A method for long-range allele-specific haplotyping of a gene in a diploid DNA sample from a single individual, wherein the method comprises:

(a) preparing a reaction mixture comprising:

(i) a diploid DNA sample containing a gene heterozygous at a first locus and at a second locus, wherein the first locus has a target allele and a variant allele that differ by a single nucleotide polymorphism, and the second locus has two alleles that differ by any polymorphism;

(ii) an allele-specific extension primer, wherein the 3' nucleotide of the allele-specific extension primer is complementary to the target allele at the position of the single nucleotide polymorphism;

(iii) a common extension primer having a sequence complementary to a remote locus common to both polynucleotide templates of the target allele and the variant allele, wherein the common extension prior encompasses the alleles of the second locus and has the opposite orientation relative to the first extension primer;

(iv) a dNTP mixture; and
(v) a polymerase enzyme having 3'→5' exonuclease activity;
(b) amplifying the polynucleotide segment under polymerase chain reaction conditions, wherein the annealing temperature is between about 5° C. and about 11° C. greater than the predicted annealing temperature for the allele-specific extension primer and its complementary sequence, thereby selectively effecting hybridization of the first extension primer to the target allele and extension of the primer, relative to the variant allele;
(c) detecting the allele of the second locus in the resulting amplification product.

2. The method of claim 1, wherein the annealing temperature is between about 8° C. and about 11° C. greater than the predicted annealing temperature for the allele-specific extension primer and its complementary sequence.

3. The method of claim 2, wherein the length of the amplified polynucleotide segment is greater than 10 kb.

4. A method for long-range allele-specific haplotyping of the CFTR gene in a diploid DNA sample from a single individual, wherein the method comprises:
(a) preparing a reaction mixture comprising:
(i) a diploid DNA sample containing the CFTR gene heterozygous at the R117H locus and heterozygous at the IVS-8 polyT locus;
(ii) an allele-specific extension primer having a sequence complementary to a region encompassing the R117H locus, and wherein the last 3'nucleotide is complementary to one of the 117R and 117H alleles at the R117H locus;
(iii) a common extension primer having a sequence complementary to a region common to both alleles of the IVS-8 polyT locus, wherein the common extension primers encompass the IVS-8 polyT locus and have the opposite orientation relative to the allele-specific extension primer;
(iv) a dNTP mixture; and
(v) a polymerase enzyme having 3'→5' exonuclease activity;
(b) amplifying the polynucleotide segment under polymerase chain reaction conditions, wherein the annealing temperature is between about 5° C. and about 11° C. greater than the predicted annealing temperature for the allele specific extension primer and its complementary sequence, thereby selectively effecting hybridization of the first extension primer to the target allele and extension of the primer, relative to the variant allele;
(c) detecting the allele of the IVS-8 5T locus in the resulting amplification product.

5. The method of claim 4, wherein the annealing temperature is between about 8° C. and about 11° C. greater than the predicted annealing temperature for the allele-specific extension primer and its complementary sequence.

* * * * *